United States Patent [19]

Ichimura et al.

[11] 3,986,297
[45] Oct. 19, 1976

[54] PHOTOSYNTHESIS REACTOR TANK ASSEMBLY

[76] Inventors: Shoji Ichimura, 1265-5, Ejiri, Takaoka, Toyama; Miki Ozono, 3-7-53, Kikunodai, Chofu, Tokyo, both of Japan

[22] Filed: June 27, 1975

[21] Appl. No.: 591,052

Related U.S. Application Data

[63] Continuation of Ser. No. 482,263, June 24, 1974, abandoned.

[52] U.S. Cl. .................................. 47/1.4
[51] Int. Cl.² ........................... A01G 33/00
[58] Field of Search ........................ 47/1.4

[56] References Cited
UNITED STATES PATENTS

| | | | |
|---|---|---|---|
| 2,658,310 | 11/1953 | Cook | 47/1.4 |
| 2,815,607 | 12/1957 | Schroeder | 47/1.4 |
| 2,996,429 | 8/1961 | Toulmin | 47/1.4 X |
| 3,195,271 | 7/1965 | Golueke | 47/1.4 |
| 3,303,608 | 2/1967 | Hannan | 47/1.4 |
| 3,439,449 | 4/1969 | Huff | 47/1.4 |

FOREIGN PATENTS OR APPLICATIONS

| | | | |
|---|---|---|---|
| 43-28933 | 12/1968 | Japan | 47/1.4 |

OTHER PUBLICATIONS

Algal Culture—, Burlew, Carnegie Inst. of Wash., Publication 600, 1953, pp. 64, 135, 136.

*Primary Examiner*—Robert E. Bagwill
*Attorney, Agent, or Firm*—Spensley, Horn & Lubitz

[57] ABSTRACT

A sealed double tank assembly for use in artificially cultivating photosynthetic substances such as chlorella. Accelerated growth of highly pure culture is obtained by means of a combination of a plurality of nozzles to emit mixed gases of carbon dioxide and ammonia, sources of light for intermittent application of light substantially similar to natural light, and agitator vanes for agitation of culture fluid in an inner tank, and an outer tank for temperature control.

13 Claims, 2 Drawing Figures

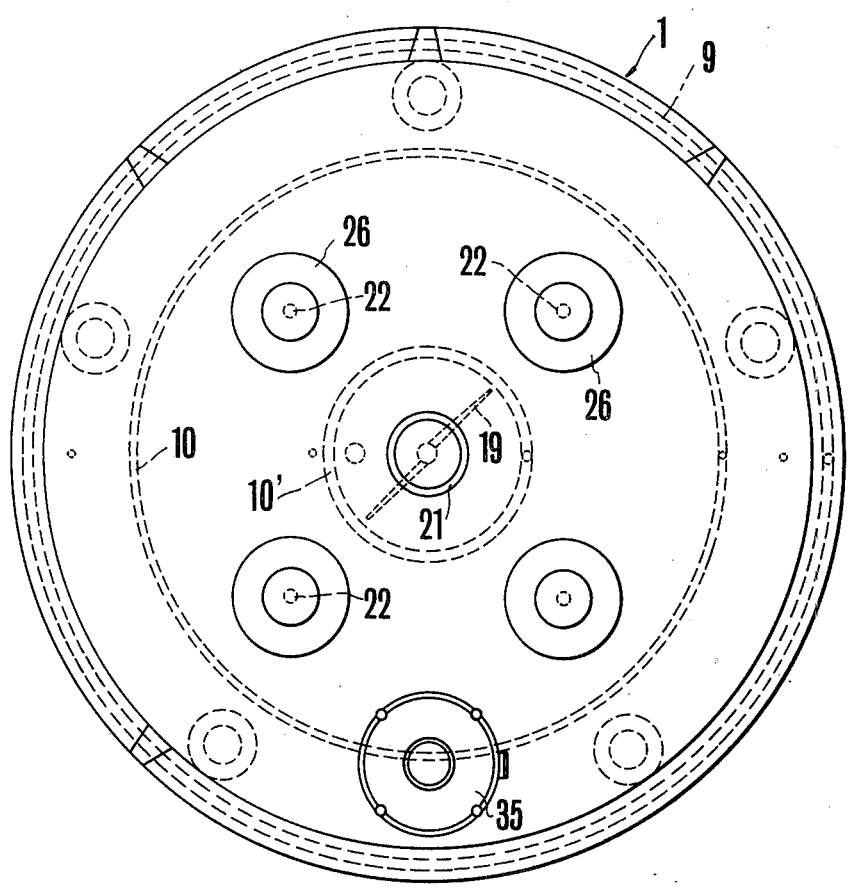

PHOTOSYNTHESIS REACTOR TANK ASSEMBLY

This is a continuation of application Ser. No. 482,263, filed June 24, 1974 (now abandoned).

BACKGROUND OF THE INVENTION

1. Field of the Invention

The present invention relates to a photosynthesis reactor tank assembly, and more particularly to a sealed double-tank assembly having an inner tank and an outer tank.

2. Prior Art

The prior art methods for artificially cultivating green algae of the photosynthesized type, particularly such as chlorella, may generally be classified into two type of processes: (1) the composite process in which the culture is grown in an outdoor pool by introducing a supply of organic acids, such as acetic acid, as the carbon source followed by applicaton of natural light, and (2) the autotrophic process in which the culture is grown in a tank by introducing glucose as the carbon source without application of light. Chlorella cultivated by the latter process has a protein composition substantially poorer than that of chlorella cultivated by the former process and is noticeably poorer in terms of yielding substances which promote microbic growth and cell-activating substances, referred to as physiologically active substances of chlorella. Thus, it is obvious that the culture of chlorella is preferably conducted with the application of light.

The composite process, however, has various drawbacks such that (1) the culture fluid may be contaminated with bacteria and the like contained in the atmosphere and the rainwater, (2) culture conditions are dictated by the weather, (3) a relatively large area is required to hold the culture fluid, the depth of which must be limited to less than 30 centimeters for a uniform light application, (4) utilization of carbon dioxide as a nutrient source is relatively low, (5) automatic control of the culture is very difficult, and (6) erosion of a culture pool may lead to deterioration of chlorella.

According to a most commonly used process, the chlorella culture fluid base substantially consists of inorganic salts and, even when urea is used as a nitrogen source, a noticeable amount of bacteria is detected. Furthermore, the chlorella culture fluid of such type may often be contaminated with heavy metals or the like contained in the rainwater which has passed through the contaminated atmosphere. Although the amount of bacteria may be reduced under heat treatment by such means as a plate heater, this treatment may also reduce nutritive qualities or desired effects of chlorella. In addition, it is practically impossible to remove heavy metal contaminants. During the night, photosynthesis will not progress without light and the growth of effective ingredients is also reduced, since the atmospheric temperature becomes lower than in the daytime, whereby the organic ingredients previously synthesized in the daytime may be consumed and the growth of chlorella is suppressed. Additionally, in order to prevent chlorella from perishing, air supply must be maintained by agitation even during the night, which would be uneconomical. The light application in the daytime varies dependent upon the weather and season and a continuous light application on the other hand would deteriorate the growth speed, the carbon utilization rate and the light energy utilization rate of chlorella, even when the amount of light to be applied may be appropriate.

To improve these adverse factors, the light application should be effected intermittently. Although a large pool may be constructed to achieve uniform application of light to the culture fluid, such a large pool increases cost, is readily contaminated with the atmosphere and the rainwater, and makes the agitation of the culture fluid difficult. As the utilization rate of carbon dioxide is too low to be practically used as the carbon source in the culture pool, acetic acid of high purity is used. However, this is very expensive. Although acetic acid may be replaced by substances such as glucose, fructose, mannose and maltose, these substances may facilitate growth of bacteria and thereby suppress the growth of chlorella. If these substances are used, the culture fluid once used cannot be repeatedly used. In addition, since chlorella may perish at pH less than 6, a very strict pH control is required around pH6.

The process mentioned above requires an examination and recording of atmospheric temperature, water temperature, pH value, PCV value, water depth, ratio of dead cells, degree of contamination, amount of sunshine, amount of rainfall and dry weight of algae several times daily for quality control, all of which makes automatic control expensive and difficult. In view of the fact that most culture pools are those of concrete, lixivium likely resulting from possible erosion of the concrete surface thereof enters into the bodies of chlorella, deteriorating the quality thereof, and causing them to die. The dead cells of clorella will emit an offensive odor. This requires frequent cleaning of the culture pool.

BRIEF SUMMARY OF THE INVENTION

This invention provides a sealed double tank assembly comprising an inner tank containing culture fluid and an outer tank in which water is circulated for temperature control. The inner tank is provided with a plurality of nozzles which emit nutrients such as mixed gases of carbon dioxide and ammonia, one or more sources of light substantially similar to natural light for intermittent light application to the interior of the tank assembly, and agitator vanes to agitate the culture fluid.

Thus, it is an object of this invention to provide a photosynthesis reactor tank in which green algae such as chlorella of excellent protein composition, high purity and cleanliness may be grown rapidly.

Another object of this invention is to provide a photosynthesis reactor tank in which chlorella may be cultivated at a low cost.

Still another object of this invention is to provide a photosynthesis reactor tank in which an automatic control may be easily achieved.

A further object of this invention is to provide a photosynthesis reactor tank which is effectively used for photosynthesizing substances such as vitamin D and polypeptide.

The novel features which are believed to be characteristic of this invention, together with further objects and advantages thereof, will be better understood from the following descripton considered in connection with the accompanying drawings in which a presently preferred embodiment of this invention is illustrated by way of example. It should be noted, however, that the drawings are for the purpose of illustration and descripton only and are not intended as a definiton of the limits of this invention.

BRIEF DESCRIPTION OF THE DRAWINGS

FIG. 2 shows a plan view of the same embodiment of this invention.

DETAILED DESCRIPTION OF THE INVENTION

Figure 1:
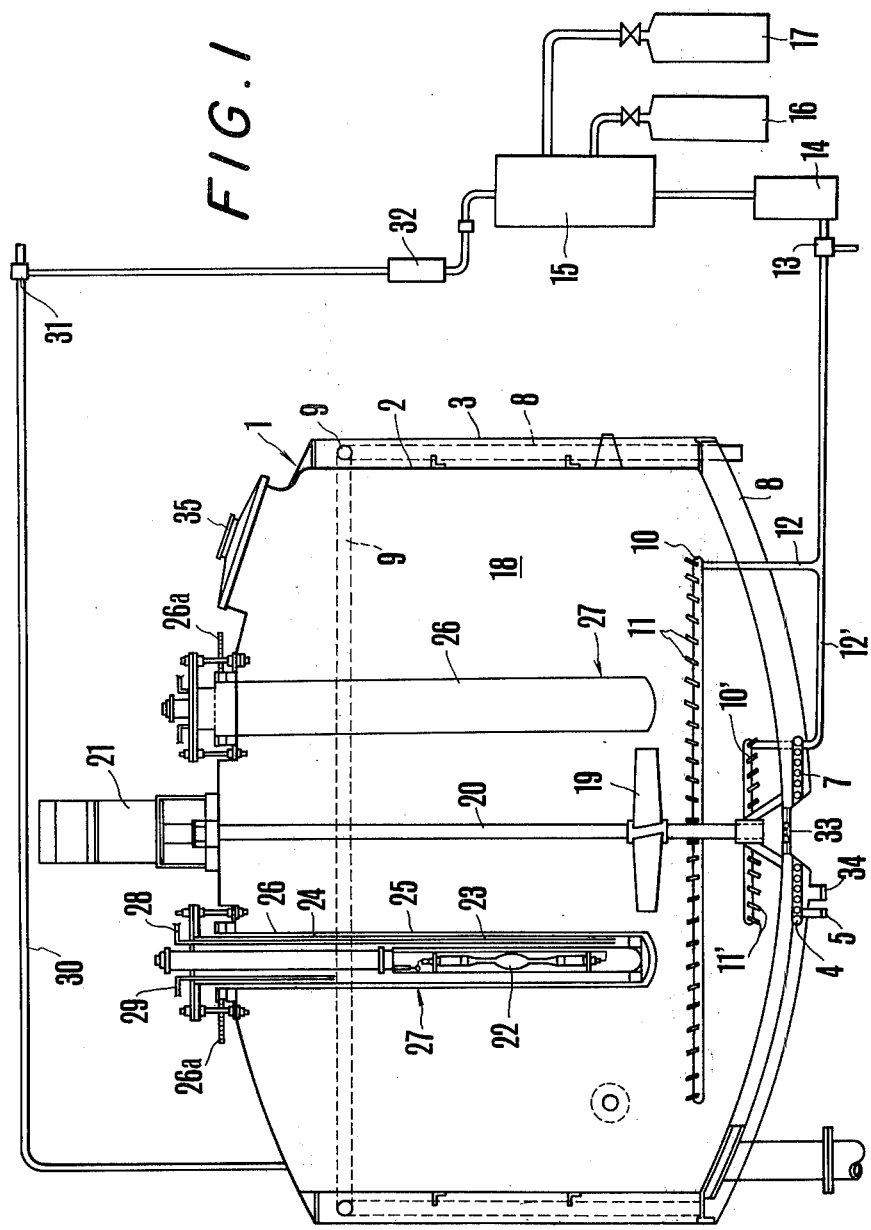
FIG. 1 shows a sectional side view of an embodiment of this invention.

The present invention will now be described more in detail with respect to a preferred embodiment as illustrated by the accompanying drawings.

Referring to FIG. 1, sealed double tank assembly 1 comprises cylindrical inner tank 2 and cylindrical outer tank 3. Annular water pipe 4 is arranged at the bottom of said outer tank 3, so that water supplied by means such as a pump is introduced into joint 5 of said water pipe and radially emitted from the bottom dioxide space 3 defined between inner tank 2 and outer tank 3 through a plurality of openings 7 formed through said water pipe 4. Overflow pipe 9 is arranged in the upper portion of said space 8 for drainage of water supplied through water pipe 4. Annular gas emitter pipe 10 with a larger diameter is provided with nozzles 11 directed obliquely downward. Two air pipes 12 and 12' adapted to supply air flow into said emitter pipes 10 and 10', respectively, are joined with each other outside sealed tank assembly 1 and connected to a gasmixing chamber 15 through a safety valve 13 and blower pump (or compressor) 14. Carbon dioxide bomb 16 and ammonia bomb 17 are connected to said gas-mixing chamber 15 in which the two types of gas from said bombs 16 and 17 are mixed and then emitted in the form of fine bubbles into culture fluid 18 in the inner tank 2 through nozzles 11 and 11' so that these gases can be mixed with inorganic nutrients. Agitator vanes 19 for agitation of culture fluid 18 in the inner tank 2 are driven by electric motor 21 through rotary shaft 20. Light source 22 is made of a xenon lamp, for example, which is substantially similar to the natural light. The embodiment as illustrated by FIG. 2 has four sources 22 arranged substantially in the middle of the depth of inner tank 2 and each of these light sources 22 is accommodated within a double cylinder assembly 27 comprising an inner cylinder 24 which hangs down in said inner tank 2 and has a transparent portion 23, and a rotatable outer cylinder 26 which has a slit 25. Each light source 22 is fixedly mounted on the inner cylinder 24 which is, in turn, secured to inner tank 2. Each outer cylinders 26 is rotated by gear 26a which is, in turn, driven by a drive (not shown) so that light emitted from said light source 22 may be intermittently applied to various spots within inner tank 2. Inlet pipe 28 and outlet pipe 29 for cooling water are inserted into the space in inner cylinder 24 so that the heat generated from the respective light source 22 may be effectively prevented by said cooling water from being transmitted into inner tank 2. Cylinder assembly 27 may be transparent and stationary while light source 22 may be intermittently energized so that chlorella in inner tank 2 can be exposed to intermittent application of light emitted from said light source 22 thereby accelerating its growth. Circulating pipe 30 is adapted to return gases accumulated within inner tank 2 during the culture process to mixing chamber 15. Safety regulator valve 31 and gas concentration detector 32 are arranged in said pipe 30.

Inner tank 2 has outlet port 33 and outer tank 3 has drain port 34 and manhole 35.

The tanks 2 and 3 as seen in FIG. 1 can be made of any material which does not interfere with the growth of the algae. For example, metal, plastic or concrete tanks may be used in the presently preferred embodiment.

We claim:

1. A photosynthesis reactor tank assembly for green algae constructed in the form of a sealed double tank assembly comprising:
    a. an inner tank in which culture fluid is accommodated, said inner tank being provided with (i) at least one means for emitting nutrient sources; and (ii) at least one light means for providing said fluid with a predetermined amount of light substantially similar to natural sunlight, said light means being disposed within and coupled to said inner tank so as to be suspended in said fluid, said light means comprises an inner cylinder disposed within an outer cylinder, said inner cylinder containing a light source and having a transparent portion, and said outer cylinder having a slit and being rotatable about said inner cylinder such that when said transparent portion is in alignment with said slit, light exits from said light means and contacts said fluid, and when said transparent portion is not in alignment with said slit, substantially no light exits from said light means; and
    b. an outer tank encasing said inner tank and provided with a means for temperature control of said fluid, said means for temperature control disposed between said inner and outer tanks.

2. A photosynthesis reactor tank assembly according to claim 1, wherein the nutrient sources comprise carbon dioxide and ammonia gases.

3. A photosynthesis reactor tank assembly according to claim 1, wherein the means for temperature control is circulating water.

4. A photosynthesis reactor tank assembly according to claim 1, wherein the inner and outer tanks have a cylindrical shape.

5. The photosynthesis reactor tank assembly according to claim 1 wherein said light source is a Xenon lamp.

6. The photosynthesis reactor tank assembly according to claim 1 wherein a coolant is disposed between said inner cylinder and said outer cylinder such that heat from said light source is removed from said light means.

7. The photosynthesis reactor tank assembly according to claim 1 wherein, in addition thereto, an agitator means for agitating said fluid is disposed within said inner tank.

8. The photosynthesis reactor tank assembly according to claim 1 wherein said means for emitting nutrient sources is formed of a first pipe having a plurality of nozzles for emitting said nutrient sources.

9. The photosynthesis reactor tank assembly according to claim 8 wherein said means for emitting nutrient sources further comprises a second pipe having a plurality of nozzles for emitting said nutrient sources.

10. A photosynthesis reactor tank assembly for algae comprising:
    a. a first tank having temperature control means disposed thereabout, said first tank adapted to contain a culture fluid for producing said algae and being provided with (i) at least one means for emitting nutrient sources; and (ii) at least one light means for providing said fluid with a predetermined amount of light substantially similar to natural sunlight, said light means extending from the exterior of said tank into the interior thereof so as to be coupled to and suspended from said first tank into said fluid, said light means comprises an inner cylinder disposed within an outer cylinder, said inner cylinder containing a light source and having a transparent portion, and said outer cylinder having a slit and being rotatable about said inner cylinder such that when said transparent portion is in alignment with said slit, light exits from said light means and contacts said fluid, and when said transparent portion is not in alignment with said slit, substantially no light exits from said light means.

11. The photosynthesis reactor tank assembly according to claim 10 wherein a coolant is disposed between said inner cylinder and said outer outer cylinder such that heat from said light source is removed from said light means.

12. The photosynthesis reactor tank assembly according to claim 11 wherein means for supplying and removing said coolant is disposed from a position exterior to said first tank through said first tank and into said light means such that said heat from said light source may be substantially removed from said interior of said first tank.

13. The photosynthesis reactor tank assembly according to claim 10 wherein, in addition thereto, a second tank is disposed about said first tank such that said temperature control means is disposed therebetween.

* * * * *